United States Patent [19]

Komori et al.

[11] 4,313,935

[45] Feb. 2, 1982

[54] ANTIBIOTIC FR-900129 SUBSTANCE, A PROCESS FOR THE PREPARATION THEREOF AND PHARMACEUTICAL COMPOSITIONS CONTAINING THE SAME

[75] Inventors: Tadaaki Komori, Takatsuki; Michio Yamashita, Takarazuka; Eiko Iguchi, Osaka; Masanobu Kohsaka, Sakai; Hatsuo Aoki, Ikeda; Hiroshi Imanaka, Osaka, all of Japan

[73] Assignee: Fujisawa Pharmaceutical Co., Ltd., Osaka, Japan

[21] Appl. No.: 125,486

[22] Filed: Feb. 28, 1980

[30] Foreign Application Priority Data

Mar. 5, 1979 [GB] United Kingdom ............... 07608/79

[51] Int. Cl.$^3$ .................... A61K 35/00; C12P 13/00
[52] U.S. Cl. .................... 424/115; 435/128; 435/136; 435/169; 435/886
[58] Field of Search ............... 435/128, 136, 169; 424/115

[56] References Cited

U.S. PATENT DOCUMENTS 4,169,888 10/1979 Hanka et al. ................... 435/128 X Primary Examiner—Lionel M. Shapiro
Attorney, Agent, or Firm—Dayton R. Stemple, Jr.

[57] ABSTRACT

Prodn. of FR-900129 comprises culturing a Streptomyces n. 4012 category which is analogous to *Streptomyces misakiensis* and *Steptomyces aburaviensis*, i.e. *Streptomyces avellaneus* No. 4012, at 25° C. to 30° C. during 50 to 100 hours in a culture medium which consists of a carbon source (e.g. glucose, fructose, glycerin, starch, galactose, maltose, dextrin), an organic or inorganic nitrogen source (e.g. yeast extract, peptone, cottonseed cake, soyabean powder, cornsteep liquor, dry yeast, ammonium nitrate, ammonium sulphate, ammonium phosphate, urea and amino acid) and an inorganic salt (e.g. calcium carbonate, sodium phosphate, potassium phosphate, sodium chloride, potassium chloride, magnesium salt and copper salt). The produced FR-900129 is isolated by a collecting step, a purifying step, a vacuum condensation step, a freeze-drying step, a pH adjusting step, a cationic, anionic or nonionic resin treating step, an active carbon adsorption step and a crystallizing and recrystallizing step. The isolated material may then be converted to its adduct salt or its ester conventionally.

9 Claims, 2 Drawing Figures

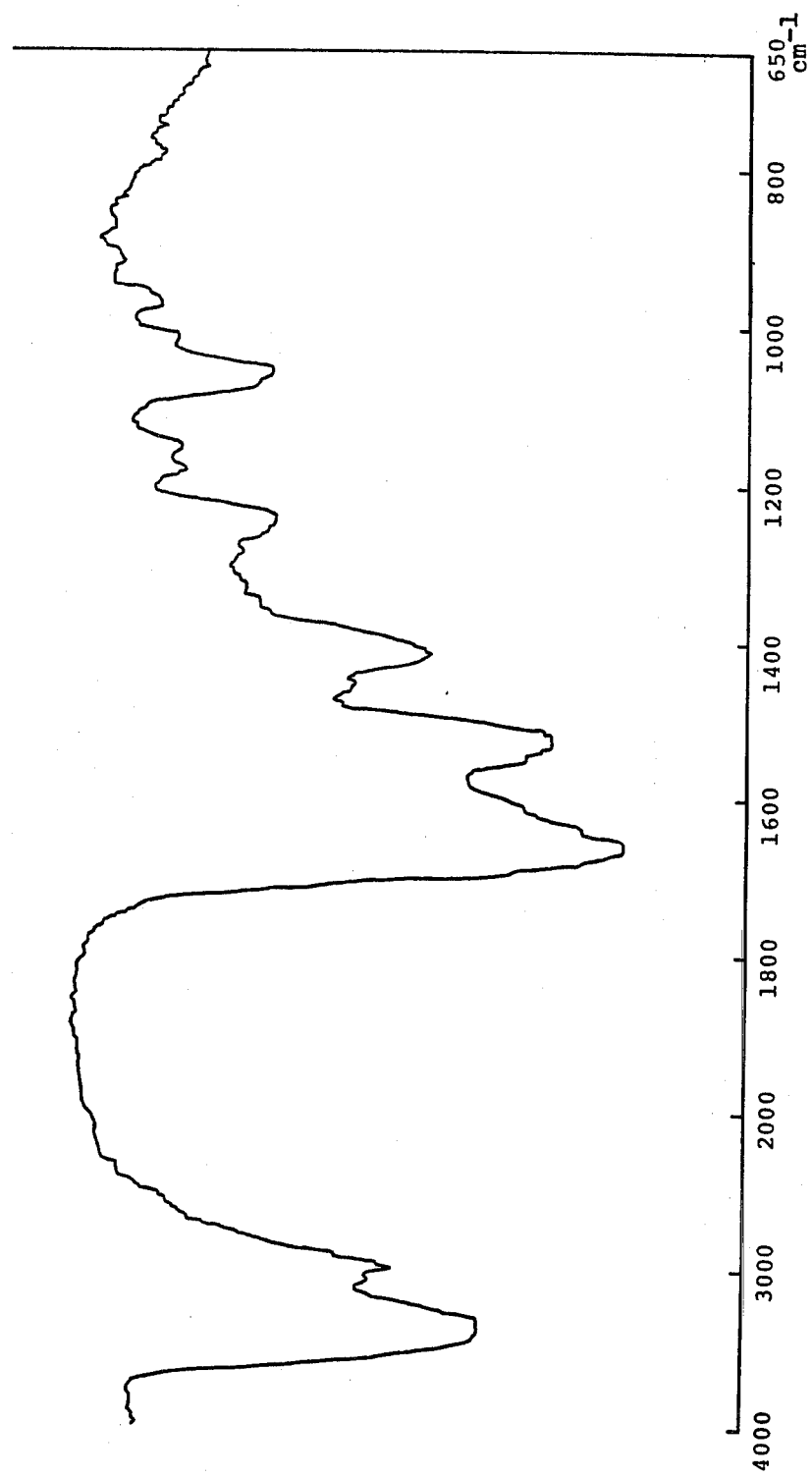
Fig. 1 Infrared absorption spectrum (KBr)

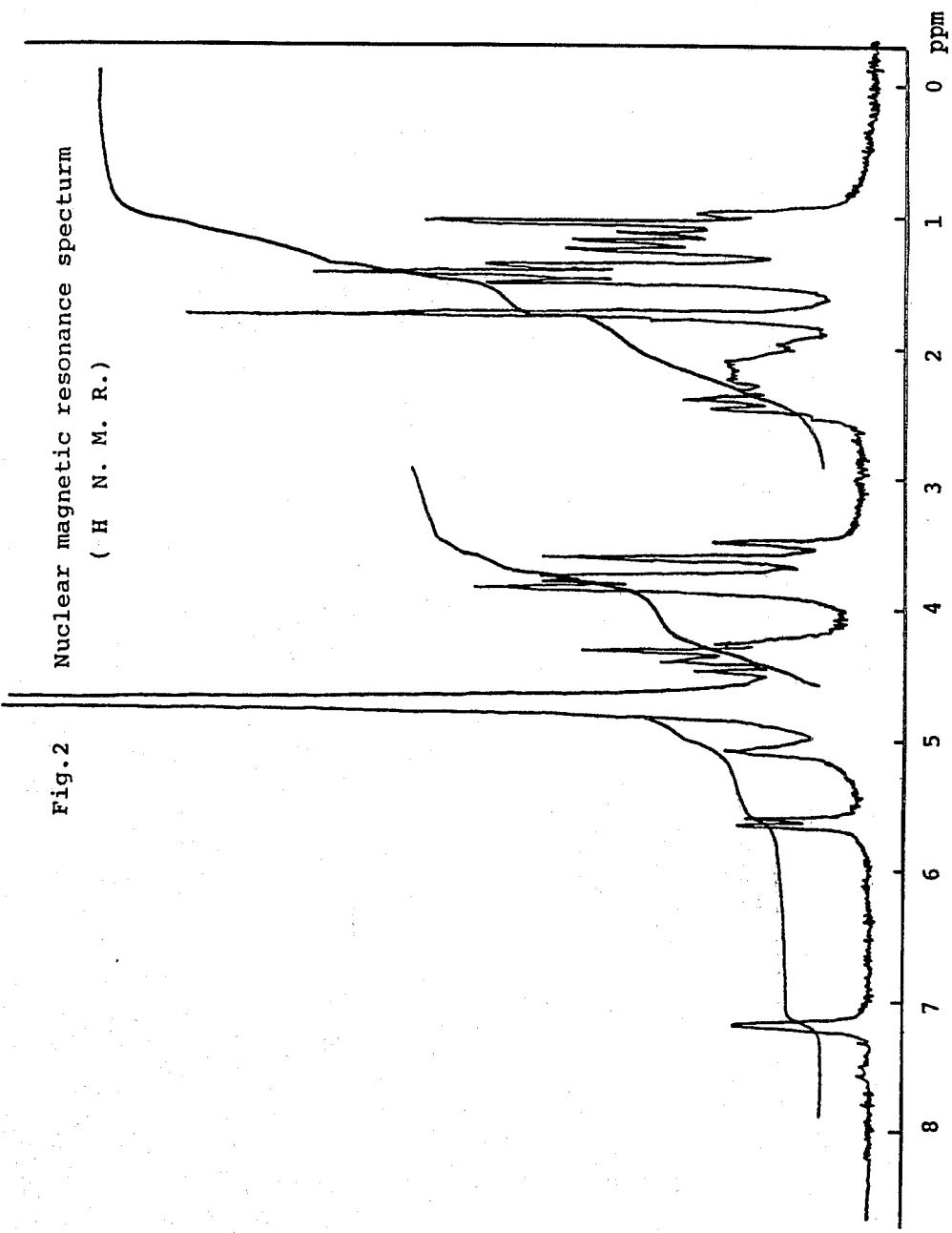
Fig. 2  Nuclear magnetic resonance specturm (H N.M.R.)

ANTIBIOTIC FR-900129 SUBSTANCE, A PROCESS FOR THE PREPARATION THEREOF AND PHARMACEUTICAL COMPOSITIONS CONTAINING THE SAME

This invention is concerned with a novel compound having antimicrobial activity, hereinafter referred to as FR-900129 substance, its esters and their pharmaceutically acceptable salts, with a process for the preparation thereof and with a pharmaceutical composition containing the same.

Accordingly, it is one object of this invention to provide a novel compound, FR-900129 substance, its esters and their pharmaceutically acceptable salts which are useful for the therapeutic treatment of infectious disease caused by pathogenic microorganism, especially gram-positive bacteria (e.g., the genus Diprococcus, Streptococcus, Staphylococcus, etc.)

Another object of this invention is to provide a process for preparing of the FR-900129 substance by fermentation of a FR-900129 substance-producing strain belonging to the genus Streptomyces in a nutrient medium.

A further object of this invention is to provide a pharmaceutical composition containing, as an active ingredient, FR-900129 substance, its esters or their pharmaceutically acceptable salts.

Still another object of this invention is to provide a method using FR-900129 substance, its esters or their pharmaceutically acceptable salts for therapeutic treatment of infectious diseases in mammal caused by bacteria which are sensitive to the FR-900129 substance.

The FR-900129 substance of this invention can be produced by fermentation of a FR-900129 substance-producing strain belonging to the genus Streptomyces such as *Streptomyces avellaneus* or the like in a nutrient medium.

Particulars of microorganism used for producing FR-900129 substance and production thereof will be explained in the following.

THE MICROORGANISM

The microorganism which can be used for the production of the FR-900129 substance is a strain belonging to the genus Streptomyces, among which a strain of *Streptomyces avellaneus* No. 4012 has been newly isolated from a soil sample collected at Wadayama-cho in Hyogo Prefecture, Japan as a suitable strain of a FR-900129 substance-producing strain belonging to the genus Streptomyces.

A culture of the newly isolated living orgaism of *Streptomyces avellaneus* No. 4012 has been deposited with and added to a permanent stock culture collection of the American Type Culture Collection under the number ATCC 31462 and is hereinafter designated as *Streptomyces avellaneus* No. 4012 ATCC 31462.

It is to be understood that, for the production of the FR-900129 substance, this invention is not limited to the use of the particular organism as described herein, which is given for illustrative purpose only. This invention also includes the use of any mutants which are capable of producing the FR-900129 substance, including natural mutants which are produced by natural mutation of the organisms as well as artificial mutants which can be produced from the described organism by conventional means, such as X-rays, ultra-violet radiation, nitrogen mustard oils and the like.

*Streptomyces avellaneus* No. 4012 ATCC 31462 has the following morphological, cultural and physiological characteristics.

(1) Morphological characteristics:

Microscopic observations were made on cultures which were grown from 10 to 14 days on sucrose-nitrate agar, glycerin-asparagine agar, yeast-malt extract agar, oatmeal agar and starchinorganic salts agar. Sporophore morphology was observed on undisturbed plates cultures.

1. Type of branching of spore-forming hyphae:
   Monopodial branching
2. Form of spore-forming hyphae:
   Rectiflexibiles
   Straight to flexous spore chains are generally long with 10 to 50 spores per chain.
3. Numbers of spores:
   10 to 50 spores per chain
4. Spore surface and spore size:
   Smooth
   $0.3$–$0.8 \times 0.7$–$1.7$ micron
5. Existence of zoospore:
   Not observed
6. Existence of sporangium:
   Not observed
7. Formation of spores:
   At aerial mycelium
8. Fragmentation of substrate mycelium:
   Not observed.

(2) Cultural characteristics:

The following observations were made on cultures which were grown on various media at 30° C. for 14 days.

| Medium | Aerial mycelium | Reverse side of colony | Soluble pigment |
| --- | --- | --- | --- |
| Sucrose-nitrate agar | light gray, powdery to short cottony | colorless to pale yellow, small colonies | none |
| Glucose-aspara asparagine agar | white to light gray, short cottony | colorless to pale yellow, small colonies | trace of light brown |
| Glycerin-asparagine agar | light gray, thin short cottony | yellowish brown to brown slightly wrinkled | light brown |
| Starch-inorganic salts agar | gray, short cottony | pale yellowish brown, wrinkled colonies | trace of light brown |
| Tyrosine agar | light gray, short cottony | brown to yellowish brown wrinkled colonies | brown |
| Nutrient agar | none or very thin white, powdery | pale yellow, flat | none |
| Yeast-malt extract agar | gray, short cottony | yellowish brown wrinkled colonies | faint brown |
| Oatmeal agar | none | very scant growth | none |
| Milk | none or thin powdery | colorless, growth on surface ring | none |
| Glucose-peptone gelatin stab | none | pale yellow to colorless, growth on surface | none or trace |
| Peptone-yeast iron agar | none | pale yellow, flat | none |

(3) Biological and physiological properties:

1. Temperature requirements (on Bennett agar slant) growth from 10° C. to 37° C. (optimum 26° C.)
2. Liquefaction of gelatin (on glucose-peptone gelatin stab)
    positive (weak)
3. Hydrolysis of starch (on starch-inorganic salt agar) positive
4. Action on milk
    no coagulation, slow peptonization
5. Production of melanin (on tyrosine agar, peptone-yeast iron agar and tryptone-yeast extract broth)
    positive on tyrosine agar, tryptone-yeast extract broth negative on
    peptone-yeast iron agar
6. Utilization of various carbon compounds (on Pridham-Gottlieb basal agar medium)
    L-Arabinose: −
    D-Xylose: −
    L-Rhamnose: −
    D-Glucose: +
    D-Fructose: +
    D-Mannose: ±
    D-Galactose: +
    Sucrose: ±
    Lactose: −
    Maltose: +
    Raffinose: −
    Inulin: ±
    Cellulose: −
    Chitin: −
    Glycerin: +
    D-Mannitol: −
    Salicin: −
    Inositol: −
    Na-Acetate: −
    Na-Citrate: +
    Na-Succinate: ±
    Symbols:
    +, good utilization
    ±, doubtful utilization
    −, no utilization As a result of looking up the strain possessing the characteristics mentioned above by referring to the literature; namely, "Bergey's Manual of Determinative Bacteriology" eighth edition (1975), and "The International Streptomyces Project Reports" written by E. B. Shirling and D. Gottlieb {Cf. International Journal of Systematic Bacteriology Vol. 18, pages 69 and 279 (1968), Vol. 19, pages 391 (1969) and Vol. 22, pages 265 (1972)}, *Streptomyces avellaneus, Streptomyces misakiensis, Streptomyces aburaviensis* have been detected as species having relatively analogous characteristics to those of the strain ATCC 31462.

The strain ATCC 31462, however, is different from these analogous species in the following:

*Streptomyces avellaneus:*
A strain of this species does not produce melanin and assimilates sucrose well.

*Streptomyces misakiensis:*
A strain of this species does not produce melanin, produces reddish pigment, and assimilates sucrose and raffinose well.

*Streptomyces aburaviensis:*
A strain of this species does not produce melanin and assimilates xylose well.

As a result of the comparisons with the above known microorganisms, the strain ATCC 31462 is mostly analogous to *Streptomyces avellaneus* and accordingly can be considered a strain of *Streptomyces avellaneus*, although there are small differences between *Streptomyces avellaneus* described in the literatures and the strain ATCC 31462. Accordingly the strain of ATCC 31462 has been designated as *Streptomyces avellaneus* No. 4012.

However, it is to be noted that the strain of ATCC 31462 is a new strain in view that it produces new FR-900129 substance, while any strains of the publicly known *Streptomyces avellaneus* have not been known to produce said FR-900129 substance.

PRODUCTION OF FR-900129 SUBSTANCE

The FR-900129 substance of this invention is produced when a FR-900129 substance-producing strain belonging to the genus Streptomyces (e.g. *Streptomyces avellaneus* No. 4012 ATCC (31462) is grown in a nutrient medium containing sources of assimilable carbon and nitrogen under aerobic conditions (e.g. shaking culture, submerged culture, etc.).

The preferred sources of carbon in the nutrient medium are carbohydrates such as glucose, fructose, glycerin, starch and the like. Other sources which may be included are galactose, maltose, dextrin, and the like.

The preferred sources of nitrogen are yeast extract, peptone, gluten meal, cottonseed meal, soybean meal, corn steep liquor, dried yeast, wheat germ, etc., as well as inorganic and organic nitrogen compounds such as ammonium salts (e.g. ammonium nitrate, ammonium sulphate, ammonium phosphate, etc.), urea, amino acid and the like.

The carbon and nitrogen sources, though advantageously employed in combination, need not be used in their pure form because less pure materials, which contain traces of growth factors and considerable quantities of mineral nutrients, are also suitable for use. When desired, there may be added to the medium mineral salts such as calcium carbonate, sodium or potassium phosphate, sodium or potassium chloride, magnesium salts, copper salts and the like. If necessary, especially when the culture medium foams seriously a defoaming agent, such as liquid paraffin, fatty oil, plant oil, mineral oil or silicone may be added.

As in the case of the preferred methods used for the production of other antibiotics in massive amounts, submerged aerobic cultural conditions are preferred for the production of the FR-900129 substance in massive amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the FR-900129 substance. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. The medium, in which the vegetative inoculum is produced, is substantially the same as or different from the medium utilized for the production of the FR-900129 substance.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°-30° C., for a period of about 50 hours to 100 hours.

Thus produced FR-900129 substance can be recovered from the culture medium by conventional means which are commonly used for the recovery of other known antibiotics.

In general, most of the FR-900129 substance produced are found in the cultured broth, and accordingly the FR-900129 substance can be separated from the filtrate, which is obtained by filtering or centrifuging the culture broth, by a conventional method such as concentration under reduced pressure, lyophilization, pH adjustment, treatment with a resin (e.g. anion or cation exchange resin, non-ionic adsorption resin), treatment with a conventional adsorbent (e.g. activated charcoal, silicic acid, silica gel, cellulose, alumina), crystallization, recrystallization and the like.

The FR-900129 substance thus produced in the culture broth can be isolated in the free form, i.e., FR-900129 substance per se and when the solution or its concentrate containing the FR-900129 substance is treated with a base, i.e. with an inorganic base such as an alkali metal compound (e.g., sodium hydroxide, potassium hydroxide, etc.), an alkaline earth metal compound (e.g., calcium hydroxide, magnesium hydroxide, etc.), ammonia and the like, with an organic base (e.g., ethanolamine, triethylamine, dicyclohexylamine, etc.); or with an acid i.e. with an inorganic acid (e.g. hydrochloric acid, sulfuric acid, phosphoric acid, etc.); or with an organic acid (e.g. formic acid, acetic acid, p-toluenesulfonic acid, citric acid, tartaric acid, etc.) during operation of the processes, e.g., extraction, isolation or purification processes, the FR-900129 substance may be transformed into and isolated in the form of the corresponding salts thereof. Alternatively, thus prepared salts of the FR-900129 substance can easily be converted to the free from, i.e. FR-900129 substance per se in a conventional manner.

Further, the FR-900129 substance obtained in the free form or its ester may be converted to the corresponding salts thereof with a base or an acid as mentioned above in a conventional manner.

Accordingly, it is to be understood that this invention includes within the scope thereof the FR-900129 substance as well as esters or salts thereof as mentioned above.

FIG. 1 is an infrared absorption spectrum (KBr) of FR-900129; and

FIG. 2 is a nuclear magnetic resonance spectrum thereof.

The FR-900129 substance as obtained according to the aforementioned process possesses the following physical and chemical properties;

(1) Form and color;
   White powder
(2) Nature of substance:
   Amphoteric
(3) Color reaction:
   Positive; iodine reaction, potassium permanganate reaction, ninhydrin reaction and Elson-Morgan reaction
   Negative; sulfuric acid reaction, Molish reaction, ferric chloride reaction, Dragendorff reaction, ammoniac silver nitrate reaction, diacetyl reaction
(4) Solubility:
   Soluble; wate, methanol, ethanol
   Insoluble; isopropanol, acetone, ethyl acetate, chloroform
(5) m.p.: 178°-179° C. (dec.)
(6) Specific rotation
   $[\alpha]_D^{20} = -69.7°$ (C=0.4 in water)
(7) Ultraviolet absorption spectrum:
   $\lambda_{max}^{H_2O} = 228$ nm ($E_{1\ cm}^{1\%} = 300$)
   $\lambda_{max}^{0.01\ N\text{-}HCl} = 228$ nm ($E_{1\ cm}^{1\%} = 300$)
   $\lambda_{max}^{0.01\text{-}NaOH} = 228$ (sh) nm
(8) Infrared absorption spectrum (KBr): (FIG. 1) As shown in the Figure of accompanying drawing.
(9) Elementary analysis:
   Qualitative analysis revealed four elements: carbon, hydrogen, nitrogen and oxygen.
(10) Thin layer chromatography

| Stationary phase | Developing solvent | Rf Value |
|---|---|---|
| EASTMAN CHROMA-GRAM SHEET*1 | butanol aqueous | 0.15 |
| Silica gel Sheet Merck*2 | 75% aqueous isopropanol | 0.35 |

*1Trade name, made by Eastman Kodak Co., a kind of cellulose sheet.
*2Trade name, made by Merck & Co.

(11) Molecular weight:
   From the result of the determination of molecular weight by titration method, it is presumably noted that the molecular weight of FR-900129 substance is between 600 and 700.
(12) Nuclear magnetic resonance spectrum: ($^{13}$C N.M.R.) (Proton decoupling method)
   (D$_2$O) (ppm from TMS): 13.469, 15,410, 17.533, 17.959, 19.172, 20.506, 21.052, 27.969, 49.204, 51.145, 54.058, 58.304, 63.583, 64.675, 65.585, 122.861, 149.314, 149.736, 167.937, 171.092, 172.859, 175.402, 176.616, 177.043
(13) Nuclear magnetic resonance spectrum (H N.M.R.)
   As shown in the Figure of accompanying drawing.
   (D$_2$O) (ppm from TMSP) (FIG. 2)

As the result of analysis of the above physical and chemical properties of the FR-900129 substance, it has been confirmed that the FR-900129 substance posesses amino and carboxy group(s) in its molecule.

Under such an observation, it has been noted that the FR-900129 can be esterified by a conventional method as explained below to provide an ester of the FR-900129 substance.

Suitable example of said esters are lower alkyl ester such as methyl ester, ethyl ester, propyl ester, isobutyl ester, t-butyl ester, hexyl ester, etc., ar(lower)alkyl ester such as phenyl(lower)alkyl ester (e.g. benzyl ester, phenethyl ester, etc.) and the like.

One of the methods for esterifying the FR-900129 substance is explained in the following.

Firstly, an amino group of the FR-900129 substance is protected by an amino protecting agent.

Amino protection is conducted by reacting FR-900129 substance or its salt with an amino protecting agent.

The amino protecting agent to be used in this process may include a conventional one such as alkylcarbonic acid or its reactive derivative.

The preferable amino protecting agent is, for example, 2-lower alkoxycarbonyloxyimino-2-phynylacetonitrile such as 2-t-butoxycarbonyloxyimino-2-phenylacetnitrile or the like.

The reaction is carried out in a conventional solvent such as water, methanol, propanol, tetrahydrofuran, dioxane, methylene chloride, chloroform, or the like, or a mixture thereof.

The reaction may preferably be carried out in the presence of a base such as trialkylamine (e.g. triethylamine or the like). The reaction temperature is not critical and the reaction is usually carried out from under cooling to warming.

The amino-protected FR-900129 substance as prepared above is esterified. Esterification is carried out by reacting the amino-protected FR-900129 substance with an esterifying agent. The esterifying agent to be used may include a conventional one such as lower alkyl halide (e.g. butyl bromide, hexyl bromide etc.), ar(-lower)alkyl halide (e.g. benzyl bromide etc.) or the like, or lower alkanol (e.g. methanol, ethanol, etc.).

The reaction is usually carried out in a conventional solvent such as N,N-dimethyl formamide, dimethylsulfoxide or the like. The reaction may preferably carried out in the presence of a base such as dicyclohexylamine or the like.

The reaction temperature is not critical and the reaction is usually carried out from under cooling to warming.

FR-900129 substance, in which an amino group is protected with an amino protecting group and an carboxy group is esterified, is subjected to elimination reaction of amino protective group. The elimination of the amino protective group in this process may be carried out by a conventional method.

Suitable method for the elimination reaction may be hydrolysis in the presence of an acid such as an inorganic acid such as hydrochloric acid or organic acid (e.g. formic acid, acetic acid, trifluoroacetic acid, etc.). In case that trifluoroacetic acid is used in this reaction, the reaction is preferably carried out in the presence of cation trapping agents such as anisole.

BIOLOGICAL PROPERTIES OF THE FR-900129 SUBSTANCE

The FR-900129 substance, its esters or their pharmaceutically acceptable salts are useful for therapeutic treatment of infectious diseases caused by pathogenic microorganism, especially gram-positive bacteria in human being and animals.

As an example for showing such antimicrobial activities of the FR-900129 substance, some pharmacological test data are illustrated in the following.

Test 1. In vitro Antibacterial Activity Test

In vitro antibacterial activity was determined by the two-fold agar-plate dilution method as described below.

One loopful of an overnight culture of each test strain in Trypticase-soy broth (about $10^6$ viable cells per ml.) was streaked on heart infusion agar (HI-agar) containing granded concentrations of the FR-900129 substance, and the minimal inhibitory concentration (MIC) was expressed in terms of mcg./ml. after incubation at 37° C. for 20 hours. Tests results are shown in the following Table 1.

TABLE 1

| Test Bacteria | MIC (mcg/ml.) |
| --- | --- |
| Staphylococcus aureus 209P | 2 |
| Bacillus subtilis ATCC 6633 | 125 |
| Diplococcus pneumoniae III | 0.25 |
| Streptococcus pyogenes S-23 | 0.25 |

Test 2. Protective Efficacy in Experimental Infection in Mice.

In determining the protective efficacy against experimental infections in mice, the FR-900129 substance was dissolved and diluted in sterile water to provide two-fold concentrations of the drug for testing Male DDY-strain mice aged 6 weeks and averaging 24–26 g. in weight, were used in groups of 5 mice each. Overnight cultures of Staphylococcus aureus 1601-47 in Difco Nutrient Broth was diluted to 1/100 in fresh medium (Difco Nutrient Broth) and incubated at 30° C. with shaking. When the cell density of $1 \times 10^8$/ml. was obtained, 0.2 ml. of the culture was injected intraperitoneally.

The FR-900129 substance solution was injected subcutaneously 0.5 hours after infection at the dose level of 30, 60, 125, 250, 500 mcg./mice, respectively. Two days after the infection, the test was considered complete and survival records of that day were made. The test results are shown in Table 2.

TABLE 2

| Dose (mcg/mice) | Survival/infected |
| --- | --- |
| 500 | 5/5 |
| 250 | 5/5 |
| 125 | 5/5 |

3. Toxicity

Intravenous administration of 2,000 mg./kg of FR-900129 substance into mice did not result in any toxic symptom for 2 weeks after injection.

The pharmaceutical composition of this invention can be used in the form of a pharmaceutical preparation, for example, in solid, semisolid or liquid form, which contains FR-900129 substance, its esters or their pharmaceutically acceptable salts, as an active ingredient. in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, simisolid, or liquid form, and in addition auxiliary, stabilizing thickening and coloring agents and perfumes may be used. The active object compound is included in the pharmaceutical composition in an amount sufficient to produce the desired antimicrobial effect upon the process or condition of diseases.

For applying this composition to humans, it is preferably to apply it by intravenous, intramuscular or oral administration. While the dosage or therapeutically effective amount of the object compound of this invention varies from and also depends upon the age and condition of each individual patient to be treated, a daily dose of about 2–100 mg. of the active ingredient/kg. of a human being or an animal is generally given for treating diseases, and an average single dose of about 50 mg., 100 mg., 250 mg., and 500 mg. is generally administered.

The following examples are given for the purpose of illustrating the present invention.

EXAMPLE 1

A vegetative medium 1 (pH 7.0) was prepared from the following ingredients:

Vegetative medium 1
Soluble starch: 1% by wt.
Gluten meal: 1% by wt.
Dried yeast: 0.5% by wt.
Corn Steep Liquor: 0.5% by wt.
Tap water: q. s.

150 ml. of the medium 1 in each of three 500 ml. flasks were sterilized in conventional manner and then inoculated with a loopful culture from a stock slant of Streptomyces avellaneus No. 4012 (ATCC 31462). The organism was grown in the medium at 30° C. for 72 hours on a shaker.

Into a 200-liter Jar-fermentor, there were placed 150 liters of the vegetative medium 1 mentioned above. The medium was sterilized in a conventional manner and then inoculated aseptically with the whole volume of the vegetative inoculum culture prepared above. The organism was grown in the medium at 30° C. for 48 hours.

35 liters of the vegetative inoculum thus prepared was aseptically inoculated into a 200-liter fermentor, containing 1700 liters of the fermentation medium prepared from the following ingredients:

Fermentation medium
Soluble starch: 5% by wt.
Gluten meal: 0.1% by wt.
Dried yeast: 0.1% by wt.
Cottonseed meal: 0.1% by wt.
Soy bean meal: 0.1% by wt.
$K_2HPO_4$: 0.1% by wt.
$(NH_4)_2SO_4$: 0.5% by wt.
NaCl: 0.3% by wt.
$MgSO_4.7H_2O$: 0.1% by wt.
$CaCO_3$: 1% by wt.
Tap water: q. s.

The organism was cultured in the fermentation medium for 72 hours at 30° C. During the growth period, the broth was stirred with a propeller operating at 170 r.p.m. and sterile air was passed through the broth at a rate of 1700 liters per minute.

After the fermentation was completed, 20 kg. "Radiolite" (trade name, a filter aid material sold by Showa Chemical Company, Japan) was added to the culture broth and mixture was filtered to remove mycelia. 1500 Liters of the filtrate thus obtained was passed through a column of activated charcoal (made by Wako Junyaku Company, Japan) (800 liters) and then washed with 1500 liters of water. Elution was carried out with 300 liters of 60% aqueous acetone. The eluate was concentrated to a volume of about 120 liters.

The concentrate was passed through a column of cation exchange resin SK-1B(H+ form, 30 liters, trade name, made by Mitsubishi Chemical Industries Ltd., Japan). The column was successively washed with 60 liters of water and eluated with 120 liters of 0.5 M sodium chloride solution. The eluate was neutralized with 2.5 N sodium hydroxide solution and concentrated to the volume of 50 liters. The concentrate was passed through a column of HP-20 resin (10 liters) (trade name, made by Mitsubishi Chemical Industries Ltd., Japan) to remove salts and washed with 20 liters of water. Elution was carried out with 30 liters of 50% aqueous methanol solution. The eluate was concentrated under reduced pressure to give 50 g. of residue. The residue was dissolved into 200 ml. of 75% aqueous isopropanol solution and the solution was subjected to column chromatography on Silica gel (3,000 ml.) (trade name, made by Merck). The column was developed and eluted with 4 liters of 75% aqueous isopropanol solution. The eluate was concentrated to give 9 g. of residue. The residue was dissolved into 500 ml. of water. The solution was passed through a column of HP-20 resin (2,000 ml.), washed with 2,000 ml. of water and then eluated with 3.5 liters of 50% aqueous methanol solution. The eluate was concentrated to give 7 g. of residue. The residue was subject to column chromatography on cellulose (1,000 ml.). The column was developed and eluted with water-saturated n-butanol (1.8 liters). The eluate was concentrated to give 3.0 g. of brownish powder. The powder was dissolved into 20 ml. of water. The solution was subjected to column chromatography on DEAE-Sephadex($CH_3COO^-$ form) (100 ml.). The column was eluated with 45 ml. of water. The eluate was concentrated to give 1.5 g. of white powder. The powder was dissolved into 30 ml. of methanol.

250 ml. of diethyl ether was added to the solution to give precipitates. The precipitates were dried to give 1.1 g. of white powders of FR-900129 substance.

EXAMPLE 2

The required quantities of the FR-900129 substance were distributed into vials, each containing 500 mg of the active ingredient. The vials were sealed hermetically to exclude bacteria. Whenever the vial is required for use, 2 ml of sterile distilled water for injection is added to the vial and then the aqueous solution is administered by injection.

EXAMPLE 3

Benzyl ester of FR-900129 substance

Triethylamine (1.77 ml.) and dioxane (40 ml.) were added to a solution of FR-900129 substance (1.34 g.) in water (20 ml.). 2-tert-Butoxycarbonyloxyimino-2-phenylacetonitrile (1 g.) was added thereto and the mixture was stirred overnight. The resultant mixture was diluted with water and extracted with ethyl acetate. The aqueous layer was passed through a column of macroporous non-ionic absorption resin, HP 20 (trade name, made by Mitsubishi Chemical Industries Ltd., Japan). Elution was carried out with 50% aqueous methanol. The eluate was concentrated under reduced pressure to give powders of N-t-butoxycarbonyl substituted FR-900129 substance (1.2 g.). Yield 78%.

M.P. 148°–158° C.

I.R. (Nujol): 3300, 1660, 1520, 1250, 1170, 1060, 960, 780 $cm^{-1}$.

N.M.R. ($D_2O$) (ppm): 7.2 (1H, broad s), 5.65 (1H, m), 5.05 (1H, m), 1.8 (3H, s), 1.45 (15H, m), 1.1 (9H, m).

Dicyclohexylamine (0.4 ml.) was added to a solution of N-t-butoxycarbonyl substituted FR-900129 substance (1.54 g.) in dimethyl formamide (60 ml.).

Benzyl bromide (0.5 ml.) was added dropwise to the mixture at 0° C.

The resultant mixture was stirred for a day at ambient temperature and then filtered. The filtrate was passed through a column of HP-20. Elution was carried out with methanol. The eluate was concentrated under reduced pressure. The concentrate was dried and then subjected to column chromatography on Silica Gel (trade name, made by Merck).

The column was washed with chloroform and eluted with mixtures of chloroform and methanol to give benzyl ester of N-t-butoxycarbonyl substituted FR-900129 substance (740 mg.). To benzyl ester of N-t-butoxycarbonyl substituted FR-900129 substance (740 mg.) was added anisole (0.15 ml.) and trifluoroacetic acid (0.10 ml.) under ice cooling. The resultant solution was stirred for 1 hour at the same temperature.

After evaporation of excess trifluoroacetic acid under reduced pressure, dried diethyl ether was added to the residue to give precipitates. The precipitates were washed with diethyl ester, and diluted sodium bicarbonate solution was added thereto to neutralize. The resultant solution was passed through a column of HP-20, which was washed with 50% aqueous methanol and then eluted with methanol. The active functions were collected and concentrated under reduced pressure. The concentrate was dried to give benzyl ester of FR-900129 substance (578 mg.).

M.P. 149°–152° C.

I.R. (KBr): 3300, 2920, 1730, 1650, 1520, 1450, 1415, 1380, 1335, 1230, 1200, 1175, 1135, 1050, 1000, 960, 905, 830, 800, 720, 695 cm$^{-1}$.

N.M.R. (CD$_3$OD), δ (ppm): 7.34 (5H, m), 7.1 (1H, m), 5.8 (1H, m), 5.2 (3H, m), 1.8 (3H, s).

EXAMPLE 4

Butyl ester of FR-900129 substance

Butyl ester of FR-900129 substance was prepared substantially in a similar manner to that of Example 3.

M.P. 134°–136° C.

I.R. (KBr): 3500, 2950, 1725, 1660, 1520, 1420, 1340, 1200, 1180, 1130, 1060, 950, 910, 835, 800, 720 cm$^{-1}$.

N.M.R. (D$_2$O) δ (ppm): 7.2 (1H, m), 5.85 (1H, m), 5.2 (1H, m), 1.8 (3H, s).

EXAMPLE 5

Hexyl ester of FR-900129 substance

Hexyl ester of FR-900129 substance was prepared substantially in a similar manner to that of Example 3.

M.P. 136°–138° C.

I.R. (KBr): 3300, 2920, 1725, 1630, 1520, 1450, 1420, 1380, 1340, 1200, 1175, 1130, 1050, 1000, 960, 900, 830, 800, 720 cm$^{-1}$.

N.M.R. (CD$_3$OD), δ (ppm): 7.1 (1H, m), 5.7 (1H, m), 5.15 (1H, m), 1.8 (3H, s).

What we claim is:

1. FR-900129 substance, its ester and pharmaceutically acceptable salt thereof, wherein the FR-900129 substance has the following physical and chemical properties;
   (1) Nature of substance:
       Amphoteric
   (2) Color reaction:
       Positive; iodine reaction, potassium permanganate reaction, ninhydrin reaction and Elson-Morgan reaction
       Negative; sulfuric acid reaction, Molish reaction, ferric chloride reaction, Dragendorff reaction, ammoniac silver nitrate reaction, diacetyl reaction
   (3) Solubility:
       Soluble; water, methanol, ethanol
       Insoluble; isopropanol, acetone, ethyl acetate, chloroform
   (4) m.p.: 178°–179° C. (dec.)
   (5) Specific rotation
       $[\alpha]_D^{20} = -69.7°$ (C=0.4 in water)
   (6) Ultraviolet absorption spectrum:
       $\lambda_{max}^{H2O} = 228$ nm ($E_{1cm}^{1\%} = 300$)
       $\lambda_{max}^{0.01\ N\text{-}HCl} = 228$ nm ($E_{1cm}^{1\%} = 300$)
       $\lambda_{max}^{0.01\text{-}NaOH} = 228$ (sh) nm
   (7) Infrared absorption spectrum (KBr): (FIG. 1) As shown in the Figure of accompanying drawing,
   (8) Elementary analysis:
       Qualitative analysis revealed four elements: carbon, hydrogen, nitrogen and oxygen
   (9) Thin layer chromatography:

| Stationary phase | Developing solvent | Rf Value |
| --- | --- | --- |
| EASTMAN CHROMA-GRAM SHEET*[1] | butanol aqueous | 0.15 |
| Silica gel Sheet Merck*[2] | 75% aqueous isopropanol | 0.35 |

*[1]Trade name, made by Eastman Kodak Co., a kind of cellulose sheet.
*[2]Trade name, made by Merck & Co.

(10) Molecular weight:
       From the result of the determination of molecular weight by titration method, it is presumably noted that the molecular weight of FR-900129 substance is between 600 and 700
   (11) Nuclear magnetic resonance spectrum: ($^{13}$C N.M.R.) (Proton decoupling method)
       (D$_2$O) (ppm from TMS): 13.469, 15.410, 17.533, 17.959, 19.172, 20.506, 21.052, 27.969, 49.204, 51.145, 54.058, 58.304, 63.583, 64.675, 65.585, 122.861, 149.314, 149.736, 167.937, 171.092, 172.859, 175.402, 176.616, 177.043
   (12) Nuclear magnetic resonance spectrum (H N.M.R.) As shown in the Figure of accompanying drawing (D$_2$O) (ppm from TMSP) (FIG. 2)

2. A compound according to claim 1, wherein the compound is FR-900129 substance or its pharmaceutically acceptable salt.

3. A compound according to claim 1, wherein the compound is an ester of the FR-900129 substance.

4. A compound according to claim 2, wherein the compound is a lower alkyl ester of FR-900129 substance.

5. A compound according to claim 4, wherein the compound is butyl ester of FR-900129 substance.

6. A compound according to claim 4, wherein the compound is hexyl ester of FR-900129 substance.

7. A compound according to claim 2, wherein the compound is phenyl(lower)alkyl ester of FR-900129 substance.

8. A compound according to claim 7, wherein the compound is is benzyl ester of FR-900129 substance.

9. A process for the production of FR-900129 substance which comprises cultivating under aerobic conditions a FR-900129 substance-producing strain belonging to the genus Streptomyces avellaneus No. 4012 ATCC 31462 in a culture medium containing assimilable sources of carbon, nitrogen and inorganic salt.

* * * * *